(12) United States Patent
Adamchick et al.

(10) Patent No.: US 9,168,418 B2
(45) Date of Patent: Oct. 27, 2015

(54) PORTABLE PHYSICAL THERAPY/REHABILITATION/EXERCISE DEVICE, SYSTEM AND METHOD

(71) Applicants: Lawrence G. Adamchick, Charlotte, NC (US); Daniel L. Adamchick, Charlotte, NC (US)

(72) Inventors: Lawrence G. Adamchick, Charlotte, NC (US); Daniel L. Adamchick, Charlotte, NC (US)

(*) Notice: Subject to any disclaimer, the term of this patent is extended or adjusted under 35 U.S.C. 154(b) by 383 days.

(21) Appl. No.: 13/730,347

(22) Filed: Dec. 28, 2012

(65) Prior Publication Data

US 2013/0172155 A1 Jul. 4, 2013

Related U.S. Application Data

(60) Provisional application No. 61/581,774, filed on Dec. 30, 2011.

(51) Int. Cl.
*A61B 1/24* (2006.01)
*A63B 24/00* (2006.01)
(Continued)

(52) U.S. Cl.
CPC ......... *A63B 24/0062* (2013.01); *A63B 21/0004* (2013.01); *A63B 21/015* (2013.01); *A63B 21/0442* (2013.01); *A63B 21/1469* (2013.01); *A63B 21/1488* (2013.01); *A63B 21/1496* (2013.01); *A63B 21/157* (2013.01); *A63B 23/14* (2013.01); *A63B 71/0622* (2013.01); *G06Q 50/22* (2013.01); *A63B 21/0023* (2013.01); *A63B 21/0552* (2013.01); *A63B 21/1645* (2013.01); *A63B 23/03525* (2013.01); *A63B 23/03533* (2013.01); *A63B 23/1209* (2013.01); *A63B 23/1245* (2013.01); *A63B 2021/169* (2013.01); *A63B 2024/0065* (2013.01); *A63B 2024/0068* (2013.01); *A63B 2071/0625* (2013.01);
(Continued)

(58) Field of Classification Search
CPC .............. A61B 1/24; A61B 5/22; A63B 7/00; A63B 22/04; A63B 71/00; A63B 24/00
USPC ............. 73/379.02, 379.09, 379.01; 482/139, 482/52, 8, 72, 4, 7
See application file for complete search history.

(56) References Cited

U.S. PATENT DOCUMENTS 4,667,513 A     5/1987   Konno
4,730,829 A *   3/1988   Carlson ............................ 482/5
(Continued)

FOREIGN PATENT DOCUMENTS

AU    5675186    10/1986
DE    8620394    11/1986
(Continued)

*Primary Examiner* — Jewel V Thompson
(74) *Attorney, Agent, or Firm* — Del Vecchio and Stadler LLP

(57) ABSTRACT

A portable physical therapy/rehabilitation/exercise device is provided for evaluating the condition of a patient and for evaluating and tracking the progress made by a patient over time. The device is hand held and has an evaluation mode to determine the current condition of the patient. The device also has a manual exercise mode and a preset exercise mode. During exercises in each mode all of the data pertaining to the forces (compression, tension, torque, and the like) are all stored in the device along with other kinds of quantitative and qualitative data. The stored data may be uploaded to the internet or external computer system in order to be further analyzed. The device is suitable for use by doctors, health care providers, insurance companies and other entities having an interest in the medical condition of the user.

18 Claims, 4 Drawing Sheets

(51) Int. Cl.

| | | |
|---|---|---|
| *A63B 71/06* | (2006.01) | |
| *A63B 21/00* | (2006.01) | |
| *A63B 21/015* | (2006.01) | |
| *A63B 21/04* | (2006.01) | |
| *A63B 23/14* | (2006.01) | |
| *G06Q 50/22* | (2012.01) | |
| *A63B 21/002* | (2006.01) | |
| *A63B 21/055* | (2006.01) | |
| *A63B 21/16* | (2006.01) | |
| *A63B 23/035* | (2006.01) | |
| *A63B 23/12* | (2006.01) | |

(52) U.S. Cl.
CPC ......... *A63B2220/16* (2013.01); *A63B 2220/17* (2013.01); *A63B 2220/34* (2013.01); *A63B 2220/51* (2013.01); *A63B 2220/56* (2013.01); *A63B 2220/805* (2013.01); *A63B 2225/20* (2013.01); *A63B 2225/50* (2013.01)

(56) References Cited

U.S. PATENT DOCUMENTS

| | | |
|---|---|---|
| 4,772,015 A | 9/1988 | Carlson |
| 4,858,125 A | 8/1989 | Washizuka |
| 5,256,117 A * | 10/1993 | Potts et al. ............... 482/52 |
| 5,391,132 A | 2/1995 | Greenwald |
| 5,471,405 A | 11/1995 | Marsh |
| 5,542,676 A | 8/1996 | Howe |
| 5,577,981 A * | 11/1996 | Jarvik ............... 482/4 |
| 5,738,616 A | 4/1998 | Robertson |
| 5,919,148 A | 7/1999 | Marko |
| 6,011,481 A | 1/2000 | Luther |
| 6,129,650 A * | 10/2000 | Wedge, Jr. ............ 482/139 |
| 6,266,623 B1 | 7/2001 | Vock |
| 6,662,651 B1 * | 12/2003 | Roth ............... 73/379.02 |
| 6,668,846 B2 | 12/2003 | Meador |
| 6,689,030 B1 | 2/2004 | Leslie |
| 6,702,725 B2 | 3/2004 | Hoffman |
| 7,066,864 B2 | 6/2006 | Olkkonen |
| 7,204,814 B2 | 4/2007 | Peles |
| 7,385,514 B2 | 6/2008 | Dempsey |
| 7,416,537 B1 | 8/2008 | Stark |
| 7,493,812 B2 | 2/2009 | Andres |
| 7,854,685 B2 | 12/2010 | Cole |
| 7,963,887 B2 | 6/2011 | Ozawa |
| 7,976,444 B2 | 7/2011 | Binns |
| 2004/0214693 A1 * | 10/2004 | Piaget et al. ............... 482/52 |
| 2004/0250618 A1 * | 12/2004 | Keiser ............... 73/379.09 |
| 2005/0061072 A1 * | 3/2005 | Ambrosone ............... 73/379.02 |
| 2005/0134470 A1 | 6/2005 | Bos |
| 2005/0257818 A1 | 11/2005 | Gillebaard |
| 2006/0040799 A1 | 2/2006 | Pompile |
| 2006/0041205 A1 | 2/2006 | Ladd |
| 2006/0064042 A1 | 3/2006 | Smyser |
| 2006/0167564 A1 | 7/2006 | Flaherty |
| 2006/0206167 A1 | 9/2006 | Flaherty |
| 2007/0299371 A1 | 12/2007 | Einav |
| 2008/0153592 A1 * | 6/2008 | James-Herbert ............... 463/36 |
| 2008/0280738 A1 | 11/2008 | Brennan |
| 2009/0036276 A1 * | 2/2009 | Loach ............... 482/72 |
| 2009/0131225 A1 | 5/2009 | Burdea |
| 2009/0201172 A1 | 8/2009 | Edell |
| 2010/0022354 A1 * | 1/2010 | Fisher ............... 482/8 |
| 2010/0100013 A1 | 4/2010 | Hu |
| 2011/0082009 A1 * | 4/2011 | Ranky et al. ............... 482/8 |
| 2011/0082011 A1 * | 4/2011 | Ellis ............... 482/54 |
| 2011/0086742 A1 * | 4/2011 | Burnfield et al. ............... 482/7 |
| 2011/0118090 A1 * | 5/2011 | Ellis ............... 482/54 |
| 2011/0152032 A1 * | 6/2011 | Barnett ............... 482/5 |
| 2013/0102440 A1 * | 4/2013 | Hutchins et al. ............... 482/8 |

FOREIGN PATENT DOCUMENTS

| | | |
|---|---|---|
| EP | 1040811 | 10/2000 |
| FR | R2638340 A1 | 5/1990 |
| SU | 1732981 | 5/1992 |
| WO | 2010085752 | 7/2010 |

\* cited by examiner

FIG. 1B  SECTION A-A

PORTABLE PHYSICAL THERAPY/REHABILITATION/EXERCISE DEVICE, SYSTEM AND METHOD

CROSS REFERENCE TO RELATED APPLICATION

This application claims the benefit of U.S. provisional patent application 61/581,774 filed on Dec. 30, 2011 the entire disclosure of which is hereby incorporated herein by reference.

BACKGROUND

The present invention is a portable therapy and exercise device that provides qualitative and quantitative feedback in the fields of physical therapy, rehabilitation, and exercise science. One of the goals of the device is to rehabilitate the user or patient in a quicker and more effective manner as compared to the devices representing the current state of the art. While not intending to limit the scope of the invention, it is envisioned that the device will be suitable for individuals with hand, wrist and shoulder injuries. It is noted that the devices in the current state of the art are specific in function and are, therefore, limited in the focus of application. For example, the current state commonly has separate devices targeting range of motion, strength assessment, and development of endurance for a given kind of injury. The current invention is able to target all of these areas of need within one portable device. The current state of the art also is specific in its targeted injury type. For example, a device may specifically target wrist strength while another separate device may target wrist flexibility. The present invention is able to target both of these areas, as well as muscle endurance. This is also true for arm and shoulder injury and rehabilitation. The current invention is able to target strength, range of motion, and muscle endurance rather than having separate devices for each area. The present invention, therefore, is not limited to a specific body part or muscle group and is not limited to targeting one area of need (strength, range of motion, endurance, etcetera.).

The current state of the art in rehabilitation/physical therapy technology utilizes specific therapeutic devices to either assess the physical state of a certain muscle group or bodily system or to rehabilitate/exercise this muscle group or bodily system. These devices range from simplistic static devices to mechanical dynamic machines having either no quantitative feedback or having rudimentary performance displays. The present invention is able to collect baseline and ongoing evaluation data, as well as be able to function as a portable exercise therapy device that critiques and provides feedback on the user's exercise form and technique.

The current state of the art requires the medical professional/therapist to administer and evaluate various exercises completed by the patient or user. When the patient or user is not in the clinical setting, the professional/therapist does not currently receive any quantitative feedback as to the efficacy of how the exercises are being performed by the patient. The therapist currently relies on subjective professional judgment and subjective patient feedback in order to track progress. The metrics used are qualitative in nature, ranging from improving to not improving and the rate of the improvement. The present invention will bring forth quantitative data in order to remove the subjectivity of human opinion and clinical judgment with regard to whether or not the exercises are being performed as intended and as to the rate of progress of the patient. This data can then be added to the patient's permanent electronic medical records. The present invention, therefore, helps to contribute to the ever-evolving field of health informatics.

The present invention is a universal assessment tool and exercise device with extensive data collection capabilities. The present invention collects data for the individual (through concurrent data provided to the user during the exercise), for the professional (through feedback provided to the therapist regarding patient performance) and for the healthcare industry (by developing standardized norms to enhance the current and future state of the industry).

SUMMARY OF THE INVENTION

The portable therapy and exercise device gathers and records data relevant to rehabilitation, physical therapy, and physical exercise. It serves as a tool that provides qualitative and quantitative feedback to its user and/or a medical professional/therapist related to the exercises performed by the user. The feedback that this device provides is given to the user in real time while using the device, thus providing feedback with regard to whether he or she is performing the exercises to a set of pre-established parameters.

The present invention ensures that the user can obtain feedback even in the absence of a medical professional/therapist. The recorded data in the form of metrics is tabulated electronically by use of a microcontroller/microcomputer, which receives input from electronic sensors and outputs voltage to the clutches and other mechanical components to control the movements of the device. These metrics can then be used to provide post-exercise feedback to the professional/therapist. This post-exercise data is initially used to establish a baseline of exercise performance. As more data is collected, a trend of performance emerges. This data is important to the professional because it helps to predict the user's recovery time and/or rate of progress. This allows the professional to be able to empirically demonstrate that these pre-programmed exercises are working to rehabilitate the user's injury. The present invention, therefore, provides quantitative documentation on specific attributes intended to maximize performance and minimize recovery time. This data becomes a tangible record of the user's recovery profile in order to provide evidence that the treatment was successful. This recovery profile can then be added to the user's permanent electronic medical records.

The use of the present invention with a large sampling of patients allows professionals to pool long-term data in order to generate standardized norms and trends of healing with different kinds of injuries. This particular benefit of the portable therapeutic exercise device can be utilized, for example, by medical professionals to document treatment and progress, by insurance companies to monitor claims, by employers to assess readiness to return to work, by legal professionals to substantiate injury severity for claims, and by athletic trainers to assess fitness for athletic participation.

One of the advantages associated with the use of the present invention is that it provides for a reliable and efficient way to collect and analyze data for individual use, for professional use, and for use on a broader scale in order to benefit the healthcare industry as a whole. Other industries associated with healthcare may also be positively impacted. Another advantage of the portable therapy and exercise device is that it provides treatment integrity, ensuring that the user is performing the prescribed exercises and that he or she is doing them properly. It also provides a quantitative means for substantiating treatment progress and outcomes that is unlike the current state of the art that relies on the subjective opinion/ report from the user. Additional advantages are that the device is portable and can target multiple kinds of injuries and multiple kinds of treatment targets (strength, range of motion, endurance, et cetera). In addition, the portable therapy and exercise device can be used as both an evaluation tool and an exercise therapy device. The present invention combines both static methods of strength and endurance assessment (the potential for the muscle to do work) and dynamic methods of assessing the endurance of the muscle while in motion (the actual work done by the muscle). The present invention is also capable of collecting data on multiple levels with varying degrees of utility and impact.

The portable physical therapy/rehabilitation/exercise device comprises a main housing having a front side that defines a visual screen display opening, at least one control switch opening, at least one indicator light opening, and a main power switch opening. A removable cover is provided and is attached to the main housing. A visual display screen disposed in the visual screen display opening. The device has first and second handles that extend from the main housing in opposite directions. The first handle is movable and extends and retracts relative to the main housing in a linear motion. The second handle rotates about a central axis relative to the main housing and the first handle.

BRIEF DESCRIPTION OF THE DRAWING FIGURES

FIG. 1B is a sectional view of the portable physical therapy, rehabilitation and exercise device taken along line A-A of FIG. 1A.

DESCRIPTION

Figure 1A:
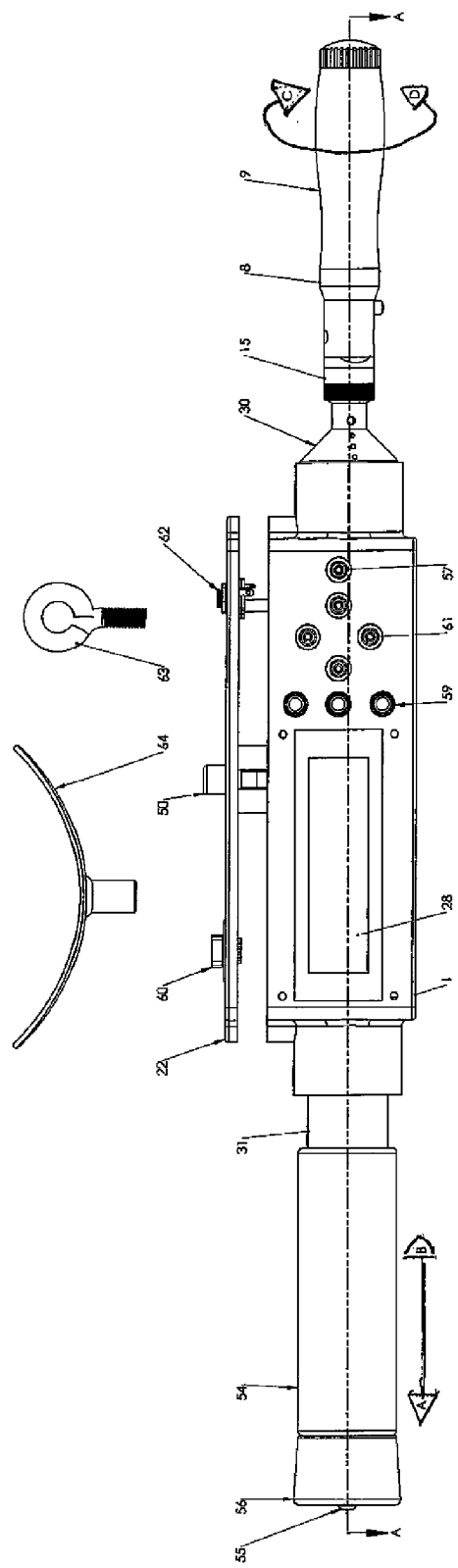
FIG. 1A is a front view of a portable physical therapy, rehabilitation and exercise device.
Figure 1A:
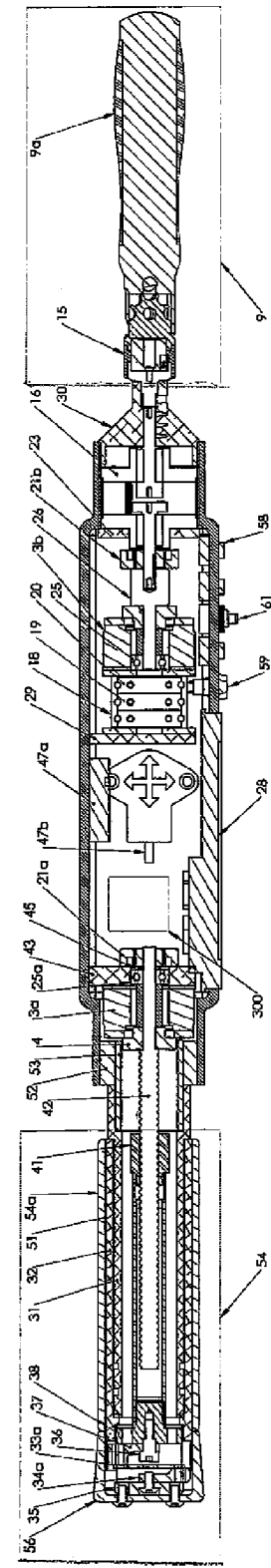

As shown in FIG. 1A, there is a portable physical therapy, rehabilitation and exercise device 100 (sometimes referred to herein as device 100). The main housing 1 of the device 100 is made of plastic, for example polyvinyl chloride (hereinafter PVC) plastic that is injection molded into the shape of the main housing 1. In other preferred embodiments, the main housing 1 is made of aluminum, metals, alloys and combinations thereof. The main housing 1 contains a portion of the internal components of the portable physical therapy/rehabilitation/exercise device 100 as will be described presently. The main housing 1 is durable and strong such that it is capable of withstanding the forces that a user (not shown) will be applying to the main housing 1 in order to protect the electronic and mechanical components disposed within the main housing 1. The front side 1e of the main housing 1 defines a visual screen display opening 1a, micro switch or control switch openings 1b, indicator light openings 1c, and a main power switch opening 1d. The main housing 1 has a generally rectangular shape, but in other preferred embodiments the main housing 1 may have a cylindrical shape or other desired shape.

The main housing 1 also contains therein electronic and mechanical components that include a programmed exercise device microcontroller/microcomputer 300 that is built into an exercise device circuit board (not shown). A visual display screen 28 (for example, liquid crystal display—LCD, light emitting diodes—LED, or any other embodiment of a visual display screen) is provided and is secured in the visual screen display opening 1a. The micro switch or control switch openings 1b provides the user with access to a plurality of control switches or buttons, such as the left, right, up and down control switches or buttons shown and commonly designated 61, that are operatively associated with the programmed exercise device microcontroller/microcomputer 300. The indicator light openings 1c allow the user to see light emitted from light emitters 59, for example, LEDs, as the user exercises. The main power switch opening 1d allows the user to access a main power switch 57 to power the device 100 on and off. A removable cover 22 is provided (see FIG. 1C) and is used to seal the top of main housing 1. The removable cover 22 also serves as a mount for a data communication port 60 and a battery charging port 62. The removable cover 22 is secured to the main housing 1 with screws, bolts or other suitable fastening mechanism (not shown). Disposed in the main housing interior are rechargeable batteries (not shown) for powering the device 100. Rechargeable batteries are well known to those having ordinary skill in the art and are, therefore, not described herein in greater detail.

Figure 1C:
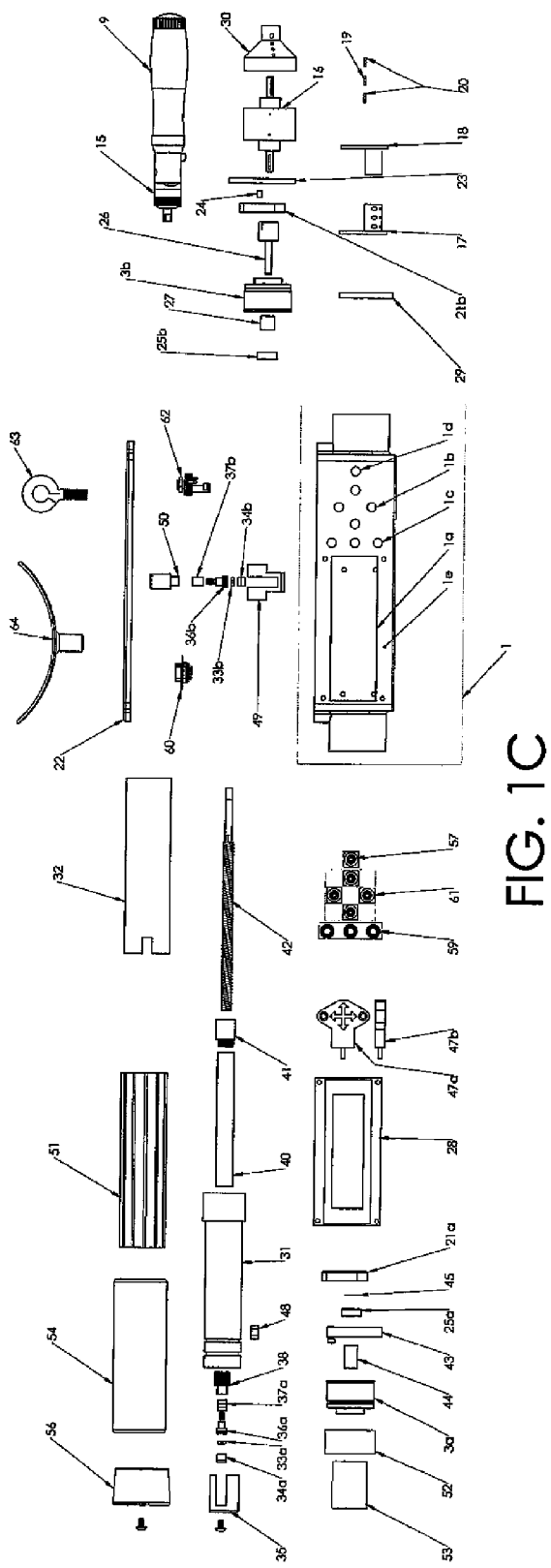
FIG. 1C is an exploded view of the portable physical therapy, rehabilitation and exercise device.

First and second handles, 54 and 9, respectively, are provided and each is proximal to the main housing 1. The first handle 54 serves to allow the user to apply mechanical force to the device 100 that is used for static and dynamic tension and compression exercises, as well as, grip compression/strength evaluations. As shown in FIGS. 1B and 1C, the first handle 54 includes a load cell strain gauge 33a that is capable of sending a signal in the form of an analog voltage output to the programmed device microcontroller/microcomputer 300. As shown in FIG. 1C, the programmed exercise device microcontroller/microcomputer 300 includes an exercise device microcontroller/microcomputer memory component (not shown) and an exercise device microcontroller/microcomputer processor component (not shown). In addition, the programmed exercise device microcontroller/microcomputer 300 is also capable of sending and receiving information via the data communication port 60 that can serve as an interface component such that it is capable of communicating with, for example, personal computers and health care provider computers (see FIG. 2). Also, it should be noted that the interface component can include any combination of hardware, firmware, or software in a computer used to enable communication or data transfer between the programmed exercise device microcontroller/microcomputer 300 and a device, system, or network external to the computer. The device 100 can connect with a system or network external to the programmed exercise device microcontroller/microcomputer 300, using, for example, wireless internet technology (Wi-Fi, 3G, 4G et cetera) connections, local area network connection (LAN) or any other connection type or protocol. All of these types of connections are well known to those having ordinary skill in the art and are, therefore, not described in greater detail herein. Microcontrollers, microcomputer, processors, memory components, circuit boards, and interfaces and their use and operation are also well known to those having ordinary skill in the art and are, therefore, not described in greater detail. In addition, the act of programming a microcontroller/microcomputer is well known to those having ordinary skill in the art and is, therefore, not described in greater detail herein.

The load cell strain gauge 33a, to be described presently, in other preferred embodiments, may be substituted for a similar device existing in the current state of the art that allows for the interpretation of force into an electronic signal. As shown in FIGS. 1B and 1C, in order for the load cell strain gauge 33a to function as a load cell, it is mounted within a load cell outer tube 32 that contains a supporting housing 35. The supporting housing 35 provides for perfectly linear motion and is disposed internal to a load cell tube inner 31. The supporting housing 35 includes load cell mounts 34a, 37a and an alignment block 38. The alignment block 38 moves within a slot within the supporting housing 35 that guides and provides for perfectly linear motion. The load cell mount 37a is allowed to turn axially with respect to the alignment block 38 due to being fastened with shoulder bolt 36a, thus further isolating the load cell strain gauge 33a from torsion loads. Alignment block 38 is mounted to ballnut mounting tube 40. The opposing end of ballnut tube 40 resides ballnut 41. Within the ballnut 41 rotates a ballscrew 42. The high mechanical efficiency of the ballnut 41 coupled to ballscrew 42 converts the linear motion of load cell outer tube 32 into a rotary motion. This rotary motion is transmitted to a first clutch assembly 3a that is supported by a bearing 25a and secured with an E-clip 45. The entire first clutch assembly 3a is mounted to the main housing 1 with a mounting bracket 43. The first clutch assembly 3a, previously described ballscrew 42, and the load cell strain gauge 33a allow a variable voltage from programmed exercise device microcontroller/microcomputer 300 to control the resistance of motion applied through the load cell outer tube 32. Clutch assemblies and the use and construction thereof are well known to those having ordinary skill in the art and are, therefore, not described in greater detail herein.

A first rotary encoder 21a is connected to the ballscrew 42 in parallel with the first clutch assembly 3a. The first rotary encoder 21a serves to provide the programmed exercise device microcontroller/microcomputer 300 with velocity and position information of load cell outer tube 32. The data input from the first rotary encoder 21a allows the programmed exercise device microcontroller/microcomputer 300 to control the voltage output to the first clutch assembly 3a, which, together, allow various modes of operation relating to the movement of load cell outer tube 32.

The user is provided with the option of selecting different modes of operation of the device 100. For example, if the static mode of operation (to be described presently) is selected, the device 100 will sense tension or compression of the load cell outer tube 32, while at the same time the first clutch assembly 3a will remain fully engaged and tension and compression forces will be sensed by load cell strain gauge 33a and no movement of load cell outer tube 32 will occur. Conversely, if the user selects the dynamic stroking mode of operation (to be described presently), the programmed exercise device microcontroller/microcomputer 300 can configure the movement of load cell outer tube 32 in a dynamic stroking mode of operation. One mode of operation consists of mechanical resistance being applied by the first clutch assembly 3a to the load cell outer tube 32 as it is moved outward (by the user) in an outward stroke (as indicated by the arrow designated A in FIG. 1A). Upon completion of the outward stroke, stroke limit is sensed by the first rotary encoder 21a, and the load cell outer tube 32 is freely allowed to stroke back (return stroke indicated by the arrow designated B in FIG. 1A) to its inward home position or its pre-stroke starting position through the release of the first clutch assembly 3a. Another mode of operation functions in the opposite manner and consists of mechanical resistance being applied by the first clutch assembly 3a to the load cell outer tube 32 as it is moved inward by the user (in the direction of arrow B). Upon completion of the inward stroke, stroke limit is sensed by the first rotary encoder 21a and the load cell outer tube 32 is freely allowed to stroke back to its outward home position (in the direction of arrow A) through the release of the first clutch assembly 3a. The friction of the first clutch assembly 3a controls the resistance of the movement of the load cell outer tube 32.

As shown in FIGS. 1B and 1C the first handle 54 also includes a handgrip sensor 51 that has in this embodiment, for example, twelve (12) flexible handgrip strain gauges that are affixed to the load cell outer tube 32. The first handle 54 includes a foam handgrip 54a that is fitted over the handgrip strain gauges 51. The user squeezes the first handle 54 with his or her hand/fingers and this creates deflections in the load cell outer tube 32 (that is made of plastic in one of the preferred embodiments). The handgrip strain gauges 51 convert these deflections into a variable voltage that is sensed and transmitted to the programmed exercise device microcontroller/microcomputer 300. The device 100 also has an end cap 56 that is connected to the first/left end of device 100, with, for example, a screw 55.

It is particularly noted that the load cell inner tube 31 supports the load cell outer tube 32 and allows the load cell outer tube 32 to move freely in a linear motion. The load cell inner tube 31 and the load cell outer tube 32 are prevented from rotating with respect to each other by an alignment key 48, which moves in the load cell outer tube 32. The load cell inner tube 31 is mounted to the main housing 1 through a mount tube 53 and a mount bushing 52. Together, the main housing 1, the mount tube 53, and the mount bushing 52 define a slot or provide clearance through which wires (not shown for the sake of clarity) are allowed to pass.

The device 100 is also capable of allowing a user to perform hand-twisting exercises. In particular, the second handle 9 is able to rotate in a twisting motion in both directions, but has a fixed linear position. The second handle 9 includes a foam handgrip 9a. These twisting motions can be used to complete hand and wrist exercises. The second handle 9 operates with a ratchet mechanism 15, such that the second handle 9 allows for forward or reverse hand twisting action, that is, clockwise (as indicated in FIG. 1A, arrow designated C) and counterclockwise (as indicated in FIG. 1A, arrow designated D) twisting of the second handle 9 relative to a longitudinal axis that extends lengthwise through the device 100 (coincident with the section-line A-A shown in FIG. 1A). The functionality of the ratchet mechanism 15 allows it to be "locked out" by the user completely to form a solid connection in which case the second handle 9 is unable to be twisted or rotated. The reversing action allows the user to complete both under and over-hand twisting exercises. The "locking out" of the ratchet mechanism 15 is used to complete static strength evaluations. For rotational exercises, mechanical resistance is applied by a second clutch assembly 3b that is fed a variable voltage by the programmed exercise device microcontroller/microcomputer 300. This allows the programmed exercise device microcontroller/microcomputer 300 to vary the degree of effort required to turn the second handle 9. A second rotary encoder 21b is connected in parallel with a second clutch assembly 3b to provide the programmed exercise device microcontroller/microcomputer 300 with velocity and positional feedback data. Disposed between the second clutch assembly 3b and the second handle 9 is a torsion load cell 19 and a gearbox 16. The gearbox 16 is mounted on a gearbox plate 23. A gearbox cap 30 is provided to protect the internal components of the device 100. The gear box 16 translates the low speed, high torque rotational movement of the second handle 9 into a higher speed, lower torque rotational movement. The purpose of this is to allow for the use of a reduced size second clutch 3b that fits into the main housing 1 due to the second clutch assembly 3b size being related to torque capacity. Between the second clutch assembly 3b and the main housing 1 is mounted a torsion load cell 19, leaf springs commonly designated 20, and first and second load cell brackets 17, 18. The torsion load cell 19 senses torque from the second clutch assembly 3b and convert the torque into an analog voltage that is then sent to the programmed exercise device microcontroller/microcomputer 300. The leaf springs 20 serve to add torsional capacity to the torsion load cell 19. The thickness of the leaf springs 20 can be varied in other preferred embodiments to adjust the maximum torque capacity of the torsion load cell 19.

In addition, as shown in FIGS. 1B and 1C, the device 100 includes an auxiliary load cell interface block 50 that is disposed in the main housing interior and serves to interface with a hook attachment 63 and a push pad attachment 64. An auxiliary load cell 33b is provided and is capable of operating in both tension and compression modes. It is similar to the previously described tension and compression load cells. However, unlike the previously described load cells that utilize load cell inner and outer tubes 31, 32 to ensure that the load cell receives a linear force, the auxiliary load cell 33b is connected to a mounting housing 49 and the auxiliary load cell interface block 50. The mounting housing 49 prevents the rotation of the auxiliary load cell interface block 50 in order for the auxiliary load cell 33b to receive a linear motion. Any small amount of rotational movement is prevented from being transmitted to auxiliary load cell 33b by a shoulder bolt 36b. The shoulder bolt 36b allows a first load cell mount 37b to be mounted to the auxiliary load cell interface block 50 while isolating rotational motion. The auxiliary load cell 33b is mounted in the first load cell mount 37b and a second load cell mount 34b. The second load cell mount 34b is mounted to the mounting housing 49 that, in turn, is mounted to the cover 22 of the main housing 1. The auxiliary load cell 33b sends a voltage signal to the programmed exercise device microcontroller/microcomputer 300 when load is applied to the hook attachment 63 or push pad attachment 64. As will be described presently, the hook attachment 63 is used in connection with a rope or elastic stretch band (not shown), where one end of the rope or elastic stretch band attaches to the device 100, and the other end is connected to a static point of attachment, for example, a wall or doorway.

As shown in FIGS. 1B and 1C, angle sensors 47a and 47b are used to sense angular input of the device 100 relative to gravity and relay this information to the programmed exercise device microcontroller/microcomputer 300. They are used for exercises where the calculation of angular movement is relevant. The sensors are also used for range of motion evaluations and data tracking. These sensors are nanomechanical (NEMS) gyroscopes in one of the preferred embodiments. There are two sensors within the body of each sensor housing, which are 47a and 47b. There are four sensors total. Only three are used to indicate the positional axes x, y, and z. Each sensor has an effective sensing range of 180 degrees when its axis is oriented within plus or minus 30 degrees relative to gravity. There is an angle sensor 47a mounted on each of the following planes in the main housing 1 interior. One of the angle sensors 47a is mounted to the bottom plane, one is mounted to the back plane, and one of the sensors 47a is mounted to the side plane of the main housing 1. The sensors 47a mounted to the bottom plane and the back plane of main housing 1 both serve to input tilt data when the user of the device 100 is tipping the device 100 from side to side. Two angle sensors 47a are called for to sense the tilt from side to side due to the fact that the main housing 1 may not always be oriented within plus or minus 30 degrees relative to gravity. To overcome this variable, the sensor 47a is mounted on the side axis of the main housing 1. It senses the axial orientation of the main housing 1 relative to gravity and based on this axial orientation from the side sensor 47a, data input is then selected from either the back sensor or the bottom sensor, whichever is in closer orientation to plus or minus 30 degrees relative to gravity. The discrimination of the selection between the bottom sensor and the back sensor is weighted proportionally as to incorporate a certain percentage of angular input data from each sensor 47a to produce an averaged signal from both sensors 47a. The side sensor 47a combines the data from the bottom sensor and the back sensor to determine the angle of the device 100 relative to gravity regardless of the axial orientation to gravity. This ensures that no matter which direction the patient tilts the device 100, even if one sensor 47a is out of range, the other sensor 47a that is in range will provide an accurate input.

The visual display screen 28 includes a self-contained driver board (not shown) that communicates using a serial communication protocol with the microcontroller/microcomputer circuit board supporting the programmed exercise device microcontroller/microcomputer 300. An electric loudspeaker (not shown), for example, Piezo, is provided on the exercise device circuit board that produces auditory tones to alert the user of various functions throughout the program and the exercise routine of the user. The main power switch 58 turns the portable physical therapy/rehabilitation/exercise device 100 on and off. The exercise device circuit board is capable of communicating with an outside or external personal computer (see FIG. 2) through data port 60 using a serial communication protocol as previously described. The battery charging port 62 is used to connect a battery charger for replenishing the batteries disposed in the main housing 1. Small screws, wiring, and other hardware are not shown for clarity, it being understood that wiring components together is well known to those having ordinary skill in the art and is, therefore, not described in greater detail herein.

Figure 2:
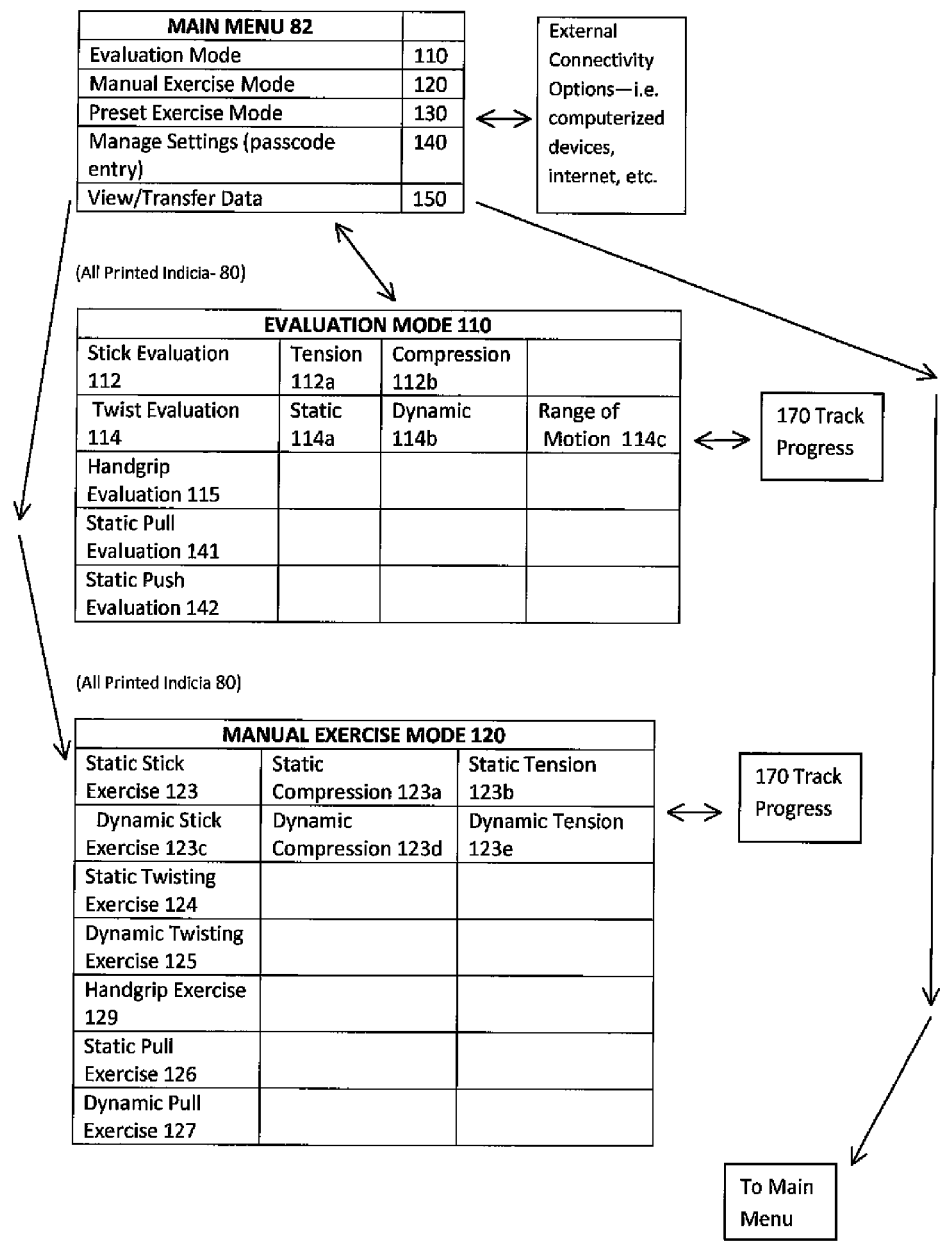
FIG. 2 is a flowchart depicting the navigational menus that appear during operation of the portable physical therapy, rehabilitation, and exercise device.
Figure 3:
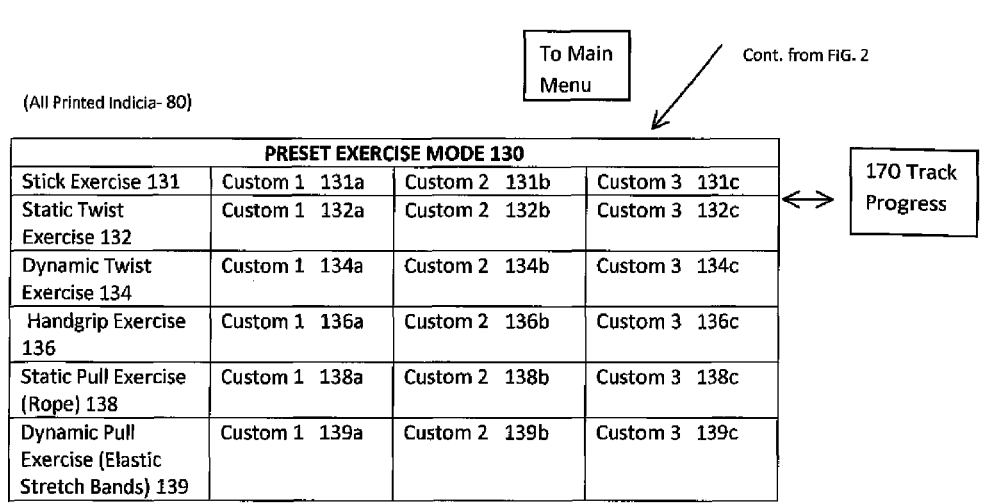
FIG. 3 is a flowchart continuing from FIG. 2.

In order for an individual to use the device 100, the user presses the main power switch 58 that may be colored red, for example, in order to power up the device 100. Shown in FIGS. 2-3 is a visual display screen 28 that displays printed indicia 80. The printed indicia 80 are in the form of words, numbers or symbols, and, as shown, there is a Main Menu 82 screen display. The Main Menu 82 displayed on the visual display screen allows the user to access one of the five main operations of the device 100. The left and right control switches 61 extending from the front of the main housing 1 allows the user to scroll through the menu selections to choose an operating mode. As shown in FIGS. 2 and 3, the five primary operating modes of the device 100 are:

Evaluation Mode 110,
Manual Exercise Mode 120,
Preset Exercise Mode 130,
Manage Settings Mode 140, and,
View/Transfer Data Mode 150.

It is pointed out that each of these primary operating modes are displayed on the visual display screen 28 as the user scrolls through the five primary operating modes by pressing the control switches 61.

As shown in FIG. 2, in Evaluation mode 110 the user will be doing a set number of sample exercises in order to establish baseline data to create guidelines for the exercises that will be represented in his or her treatment plan. For static tension or compression evaluations, the user will choose Stick Evaluation 112 and will be prompted to choose tension 112a or compression 112b on the visual display screen 28. The user then begins the evaluation mode by pushing inward or pulling outward (tension or compression) on the first and second handles 54, 9 as hard as he or she can for as long as he or she can (or until it starts to feel uncomfortable). This represents one repetition. The user is then given the opportunity to repeat this action for a set number of trials. This data is then assigned certain values that are stored in exercise device microcontroller/microcomputer memory component. The stored parameter data will include the mode utilized (Evaluation mode) and the type of exercise (stick tension or stick compression). Quantitative data recorded will include the maximum force exerted, the number of repetitions, and the time (in seconds) that it took the user to reach the maximum force for a given repetition.

In Manual Exercise Mode 120, the user selects Static Stick Exercise 123. The user then inputs the type of force (static compression 123a, static tension 123b, or both), the number of repetitions, the amount of force (pounds/kilograms), and the desired hold time (in seconds). After this data is entered, the exercises may commence. This data must be entered every time the user wants to use this manual setting mode. During this mode, the first handle 54 remains fixed and only static force data is sensed. The user begins the repetition by applying force to the device 100 (either tension or compression) until he or she reaches the set force threshold. The user will then hear a beep generated by the device 100 and will be prompted to hold the set force for the indicated hold time. The user then will be prompted to release the force. The user repeats the exercises until he or she completes the set number of repetitions. If the user applies too much force or not enough force during the requisite hold time, the device 100 will indicate this on the visual display screen 28, and will produce an audible sound and will prompt the user to start that particular repetition over again. This concurrent feedback allows the user the opportunity to retry the repetition and progress through the remainder of the repetitions.

When the repetitions are all completed the Track Progress 170 screens will be displayed. The user is then presented with post-exercise feedback on the repetitions performed and the data set is given a unique serial number. The data saved in the microcontroller/microcomputer memory component of the device 100 will include the mode utilized (Manual Exercise 120) and the type of exercise (static compression 123a, static tension 123b, or both). Additional parameter data recorded includes the set force units and the target hold time (in seconds). The quantitative data collected includes the number of ideal repetitions and the number of times that the user went over or under the set force. A derived score is then calculated by the programmed exercise device microcontroller/microcomputer 300 on force units under or over the target force and on the number of hold time failures. A perfect score is obtained when the user optimally completes the repetitions with the prescribed force for the full hold time. The score is recorded as well as the breakdown of the score: Perfect repetitions, under-force repetitions, and over-force repetitions and saved in the exercise device microcontroller/microcomputer memory component so that it can be accessed in the future.

In Manual Exercise Mode 120 the user can also select Dynamic Stick Exercise mode 123c. During this mode, the user must input the type of resistance (dynamic tension mode 123e-outward stroke, dynamic compression mode 123d-inward stroke, or both) and the number of repetitions. In the dynamic tension mode 123e, the user begins with the first handle 54 in the inward position (the handle is in a compressed state) and applies tension with the first handle 54 (while holding the second handle 9) and strokes to the outward position with the resistance having been preselected by the user. The stroke is completed when the limit of travel is reached. It is then free to return to its home inward position. In the dynamic compression mode 123d, the user starts with the first handle 54 in the outward position and applies compression force while the first handle 54 strokes to the inward position with the resistance preselected by the user. The stroke is completed when the limit of travel of reached. It is then free to return to its home outward position. The user continues until the preset number of repetitions is completed.

When the repetitions are all completed the Track Progress 170 screens will be displayed on the visual display screen 28. The user is then presented with post-exercise feedback on the repetitions performed and the data set is given a unique serial number. The data saved in the device microcontroller/microcomputer memory component includes the mode utilized (Manual Exercise 120) and the type of exercise (stick tension, stick compression, or both). Additional parameter data recorded will include the set force/resistance units. The quantitative data collected will include the number of ideal repetitions. An ideal repetition is a stroke with a short acceleration and a constant motion profile. A derived score will be calculated by the programmed exercise device microcontroller/microcomputer 300 and will be based on how constant the motion is of the completed strokes. A perfect score is obtained when the user optimally completes the repetitions with fluid stroking (continuous smooth movements) at the desired resistance level.

The Preset Exercise Mode 130 shown in FIG. 3 is similar to the Dynamic Stick Exercise mode 123c of the Manual Exercise mode 120, except the user selects from three preset exercises pre-programmed into the programmed exercise device microcontroller/microcomputer 300 of the device 100 by an administrator or medical professional. The user selects Preset Exercise Mode 130 from the main menu 82 and the visual display screen 28 displays the options shown in FIG. 3. The user selects Preset Dynamic Stick Exercise 131 and is allowed to choose one of the preset exercises generally designated Custom 1, Custom 2, and Custom 3 (131a, 131b, 131c, respectively) by depressing the left and right buttons 61 that protrude from the front side 1e of the main housing 1. The results of the exercise performed in this operating mode are stored in exercise device microcontroller/microcomputer memory component as described above. The exercises' parameters are preset by the administrator and cannot be modified by the user.

For twisting type evaluations, the user selects Evaluation Mode 110 and Twist Evaluation 114 (see FIG. 2). The user is then prompted to choose from three different kinds of twisting evaluations: Strength/static 114a, dynamic 114b, and range of motion 114c. For strength/static twisting-type evaluations, the user will conduct a set number of sample trials in order to establish baseline data to create guidelines for the exercises that will be represented in his or her treatment plan. In this static mode, the second handle 9 does not rotate and this serves to input torque data through the torsion load cell 19. The user begins the static evaluation mode by holding device 100 and gripping the first handle 54 in the non-injured hand and the second handle 9 in the injured or targeted hand. The user then applies a twisting torque to the static handle with as much force as possible for as long as possible. This represents one repetition. The user is then given the opportunity to repeat this action for a set number of trials. This data is then assigned certain values that are stored in the exercise device microcontroller/microcomputer memory component of the device 100. This stored data will include the mode utilized (Evaluation mode), the type of exercise (static twist), the maximum torque exerted, the number of repetitions, and the time (in seconds) that it took the user to reach their maximum torque for a given repetition.

For dynamic twisting evaluations 114b, the torque level setting is derived from a baseline taken from the previously described strength/static evaluation exercise. It represents the maximum amount of torque that the user will be inputting into the device 100. The user grips the first and second handles 54, 9 of the device 100. The user then manually applies torque to the first and second handles 54, 9 and when the pre-set level torque threshold has been reached the second clutch 3b slips and the second handle 9 begins to rotate. The user then tries to twist the second handle 9 as far as he or she can, twisting against the resistance of the preset torque, until it is no longer comfortable. The user repeats this exercise for a set number of repetitions. The device 100 saves and records the mode of the exercise (Evaluation mode), the type of exercise (dynamic twist 114b), the time to reach the set threshold torque before movement takes place, the duration of time from when movement begins to when movement ends, and the rotation (in degrees) of the actual movement accomplished in the exercise device microcontroller/microcomputer memory component.

For range of motion twisting evaluations, the user chooses Evaluation Mode 110 and selects Range of Motion Evaluation 114c. In this mode, the second handle 9 is allowed to rotate freely in order to record the angular movement of the exercise. In this mode, the user then is prompted to grip the first and second handles 54, 9 of the device 100 in the user's most comfortable baseline position. The user is then prompted to press the button 61 to activate the program. The repetition begins when the user starts to rotate the second handle 9. This rotation continues until the user experiences mild discomfort. The user then stops the motion of rotation. This is considered one complete evaluation repetition. The user repeats this exercise for a set number of repetitions. The device 100 records the mode of the exercise (Evaluation mode), the type of exercise (range of motion) and the rotation (in degrees) of the actual movement accomplished in the exercise device microcontroller/microcomputer memory component.

For Manual Twisting Exercises when in Manual Exercise Mode 120, the user chooses either Static Twisting Exercise 124 or Dynamic Twisting Exercise 125. For strength/static manual exercise 124, the user inputs the number of force units desired and the desired hold time. Within this mode, the second handle 9 does not rotate, and all the torque applied by the user is measured by the torsion load cell 19. The exercise begins when the user applies a static torque to the first and second handles 54, 9. When the peak set torque is reached, the user will be prompted to hold the repetition for the set number of seconds. The user will then hear a beep and will be prompted to release. This is considered one repetition. The user repeats this exercise for a set number of repetitions. If the user applies too much torque or not enough torque during the requisite hold time, the device will indicate this on the visual display screen 28, and will alert the user with an audible sound, for example a beep, and will prompt the user to start that particular repetition over again. In other preferred embodiments, the device 100 may be designed to vibrate so as to alert the user. This concurrent feedback allows the user the opportunity to retry the repetition and progress through the remainder of the repetitions. When the repetitions are completed, the user will then be sent to the Track Progress screens 170 that appear on the visual display screen 28 where the user is presented with post-exercise feedback on the repetitions performed and his or her data set is given a unique serial number. The parameter data recorded is the set force units and the hold time that was inputted. The quantitative data collected will consist of the number of ideal repetitions and the number of times that the user went over or under the set torque. A derived score will be calculated by the programmed exercise device microcontroller/microcomputer 300 based on force units under or over the target torque and on hold time failures. A perfect score is obtained when the user optimally completes the repetitions with the prescribed force for the full hold time. The score is recorded as well as the breakdown of the score: Perfect repetitions, under-force repetitions, and over-force repetitions.

For dynamic twist manual exercises, the user Manual Exercise Mode 120, and then Dynamic Twisting Exercise mode 125. The user manually inputs the number of desired repetitions and inputs the number of degrees of desired rotation for the exercise via the visual display screen 28 and the buttons 61. After this data is entered, the exercises may commence. This data must be entered every time the user wants to use this manual setting mode. The user begins the repetition by applying torque to the first and second handles 54, 9 (dynamic twist) of device 100 until he or she reaches the set force threshold. Once the threshold is reached, the second clutch assembly 3b begins to slip and the handle begins to rotate. Once the set degree of rotation is reached, the user will hear a beep and he or she is prompted to release. This is considered one repetition. The user then repeats the exercises until he or she completes the set number of repetitions. The data is saved in the exercise device microcontroller/microcomputer memory component and includes the mode utilized (Manual Exercise) and the type of exercise (dynamic twist). Additional parameter data recorded will include the set degrees of rotation and the clutch torque setting. The quantitative data collected will include the number of successful repetitions and the number of failed repetitions. A derived score will be calculated by the programmed exercise device microcontroller/microcomputer 300 based on successful or unsuccessful repetitions. A perfect score is obtained when the user optimally completes the repetitions with prescribed torque for the set degrees of rotation.

The Preset Exercise Mode 130 for twisting is similar to the above-described Static and Dynamic Twisting Exercise modes 124, 125, except the user selects from three preset exercises pre-programmed into the programmed exercise device microcontroller/microcomputer 300 by the administrator/medical professional. As shown in FIG. 3, the user chooses Preset Exercise Mode 130 and then either Static Twist Exercise 132 or Dynamic Twist Exercise 134. For each type of exercise, the user chooses either Custom 1, Custom 2, Custom 3 (132a, 132b, 132c, respectively, or 134a, 134b, 134c, respectively) exercises that have been pre-programmed by the administrator/medical professional. The data recorded will be the same as described above for the Manual Static and Dynamic Twisting Exercise modes.

For handgrip strength evaluations, the user selects Evaluation Mode 110 and Handgrip Evaluation 115. The user will be doing a set number of sample trials in order to establish baseline data to create guidelines for the exercises that will be represented in his or her treatment plan. The user begins the evaluation mode by holding the device 100, gripping the second handle 9 in the non-injured hand and gripping the first handle 54 in the injured/targeted hand (hand being treated). The user then squeezes the handgrip of the first handle 54 with the injured/targeted hand with as much force as he or she is capable of exerting for as long as he or she can. This represents one repetition. The user is then given the opportunity to repeat this action for a set number of trials. This data is then assigned certain values that are stored in the exercise device microcontroller/microcomputer memory component of the device 100. This stored data will include the mode of the exercise (Evaluation mode 110), the type of exercise (grip compression), the maximum pressure that the user exerted on the handgrip of the second handle 9, and the length of time (in seconds) it took to achieve his or her maximum exerted pressure.

As shown in FIG. 2, for handgrip strength exercises in the Manual Exercise Mode 120 and then Handgrip Exercise 129. The user inputs the amount of pressure, desired hold time, and the number of repetitions. The user is then prompted to squeeze the foam handgrip 54a of the first handle 54. When the set pressure is reached, the user is prompted to hold for the set number of seconds. The user is then prompted to release the foam handgrip of the first handle 54. This is considered one repetition. The user will continue for the set number of repetitions until the series of exercises is complete. If the user applies too much force or not enough force during the requisite hold time, the device will alert the user by indicating this on the visual display screen 28, will generate an audible sound, and will prompt the user to repeat that particular repetition over again. This concurrent feedback allows the user the opportunity to retry the repetition and progress through the remainder of the exercises.

When the repetitions are all completed, the user will then be sent to the Track Progress screens 170. There the user is presented with post-exercise feedback on the repetitions performed and his or her data set is given a unique serial number. The data recorded will be stored in the exercise device microcontroller/microcomputer memory component of the device 100. This stored parameter data will include the mode of the exercise (Manual Exercise Mode 120), the type of exercise (grip compression), the set pressure, and the set hold time. The quantitative data collected will include the number of ideal repetitions and the number of times that the user went over or under the set pressure. A derived score is be determined by the programmed exercise device microcontroller/microcomputer 300 based on the number of pressure units under/over the target pressure and on hold time failures. A perfect score is obtained when the user optimally completes the repetitions with prescribed pressure for the full hold time.

For Preset Handgrip Exercise Mode 136 (FIG. 3), the user chooses Preset Exercise Mode 130 from the main menu 82 and then Handgrip Exercise 136. The user then selects from three preset exercises pre-programmed into the device by the administrator/medical professional entitled Custom 1, Custom 2, and Custom 3 (136a, 136b and 136c, respectively) by using the left and right buttons 61. The results of the exercises performed in this operating mode are stored in the exercise device microcontroller/microcomputer memory component of the device 100.

As shown in FIG. 2, for evaluations using the auxiliary load cell interface block 50, the user selects Evaluation Mode 110 and either Static Pull Evaluation 141 or Static Push Evaluation 142. For static pull 141 evaluations using the hook attachment 63, the user will be doing a set number of sample trials in order to establish baseline data to create guidelines for the exercises that will be represented in their treatment plan. The user begins the static pull evaluation mode 141 by attaching the hook 63 to the portion of the auxiliary load cell interface block 50 that extends from the main housing 1. The rope attachment is then attached to the hook 63 at one end, and the other end of the rope is connected to the static attachment point in the user's environment, for example a wall or doorway. The user grips the first and second handles 54, 9 of the portable physical therapy/rehabilitation/exercise device 100 and applies tension to the rope by pulling equally on the first and second handles 54, 9. The path of the motion can be adjusted to suit each individual user's requirements. The user pulls as hard as he or she can for as long as possible, until it begins to feel uncomfortable. This represents one repetition. The user repeats this procedure for a set number of repetitions. The device 100 records the mode of the exercise (Evaluation Mode 110), the type of exercise (static pull 141), the amount of force applied (in pounds/kilograms) in the exercise device microcontroller/microcomputer memory component.

For static push evaluations 142 using various pressure pad attachments 64, the user will be doing a set number of sample trials in order to establish baseline data to create guidelines for the exercises that will be represented in his or her treatment plan. The user begins the static push evaluation mode 142 by attaching the pressure pad attachment 64 to the auxiliary load cell interface 50. The medical professional grips the first and second handles 54, 9 for this evaluation mode and the user/patient will be pushing on the pressure pad attachment 64 with their injured/target appendage. This allows the device 100 to collect and store data pertaining to the amount of force the patient can apply before feeling discomfort. The data generated is stored in the exercise device microcontroller/microcomputer memory component.

As shown in FIG. 2, for manual exercises, the user selects Manual Exercise Mode 120 and then selects Static or Dynamic Pull Exercise Mode 126, 127 and attaches the hook 63 to the auxiliary load cell interface 50. A rope or elastic stretch band is then attached to the hook 63 with the other end of the rope or elastic stretch band attached to a static attachment point, for example a wall or doorway in the user's environment. For static pull manual exercise using the rope, the user inputs the number of force units desired and the desired hold time. For dynamic pull manual exercise using the elastic stretch bands, the user inputs the desired force units and the desired hold time. Both static and dynamic pull program modes are identical for this exercise; however, by inputting either static (rope) or dynamic (elastic stretch band) exercise mode the storage data is coded accordingly. To start the exercises, the user grips the first and second handles 54, 9 of the device and applies tension to the rope or the elastic stretch bands by pulling equally on the first and second handles 54, 9. The user will hear an audible beep or other indicator when the force threshold is reached. The user will be prompted to hold the repetition for the set hold time and then release. This represents one repetition. The path of the motion can be adjusted to suit each individual user's requirements. If the user applies too much force or not enough force during the requisite hold time, the device 100 will indicate this in some way to the user (visually on the visual display screen 28 or by an audible beep) and will prompt the user to start that particular repetition over again. This concurrent feedback allows the user the opportunity to retry the repetition and progress through the remainder of the repetitions.

When the repetitions are all completed, the user will then be sent to the Track Progress screens 170 that appear on the visual display screen 28. There the user is presented with a visual display of post-exercise feedback on the repetitions performed and his or her data set is given a unique serial number. The results are stored as data in the exercise device microcontroller/microcomputer memory component of the device 100. The parameter data recorded will include the mode of the exercise (Manual Exercise Mode 120) and the type of exercise (static pull 126 or dynamic pull 127). Additional parameter data will include the set force and the set hold time. The quantitative data collected will include the number of ideal repetitions and the number of times that the user went over or under the set force threshold. A derived score is determined by the programmed exercise device microcontroller/microcomputer 300 based on force units under/over target force and on hold time failures. A perfect score is obtained when the user optimally completes the repetitions with the prescribed force for the full hold time.

As shown in FIG. 3, the Preset Static Pull Exercise mode 138 and the Preset Dynamic Pull Exercise 139 modes are similar to Manual Static/Dynamic Pull Exercise mode 126, 127, except the user selects from three preset exercises pre-programmed into the programmed exercise device microcontroller/microcomputer 300 by the administrator/medical professional. The user chooses Preset Exercise mode 130 and then the Static Pull Exercise mode 138 (rope) or the Dynamic Pull Exercise mode 139 (elastic stretch bands). For the Static Pull Exercise 138 the user chooses either Custom 1, Custom 2, Custom 3 exercises (138*a*, 138*b*, 138*c*, respectively) that have been pre-programmed by the administrator/medical professional with the pounds of force and the desired hold time. For the Dynamic Pull Exercise 138 the user chooses either Custom 1, Custom 2, Custom 3 exercises (139*a*, 139*b*, 139*c*, respectively) that have been pre-programmed by the administrator/medical professional with the pounds of force and the desired hold time. Both static and dynamic pull program modes 138, 139 are identical for this exercise; however, by inputting either static (rope) or dynamic (elastic stretch band) exercise mode the storage data is coded accordingly. To start the exercises, the user grips the first and second handles 54, 9 of the present invention and applies tension to the rope or elastic stretch bands by pulling equally on the first and second handles 54, 9. The user will hear an audible beep or other indication when he or she reaches his or her set force threshold. The user will be prompted to hold the repetition for the desired hold time and release. This represents one repetition. The path of the motion can be adjusted to suit each individual user's requirements. The results are stored as data in the in the exercise device microcontroller/microcomputer memory component.

In Manage Settings Mode 140, the administrator is able to modify the settings of the device and edit such things as the Preset Exercise parameters (for example, Custom 1, Custom 2, and Custom 3) for each exercise mode, erase the memory of the exercise device microcontroller/microcomputer memory component of the device 100, and to switch the force mode of the device from pounds to kilograms and from foot pounds to Newton's (torque). The administrator in charge or other authorized person are the only people that can access the Manage Settings mode 140, thus a password is required to access this mode. In particular, once the Manage Settings mode 140 is selected from the Main Menu 82, a pass code entry is required to modify the settings of the portable physical therapy/rehabilitation/exercise device 100. The use of passwords to allow or deny access to computers/electronic devices is well known to those having ordinary skill in the art and is, therefore, not described herein in greater detail.

In the View/Transfer Data mode 150, the user can view the previously recorded set records and transfer this data out of the exercise device microcontroller/microcomputer memory component of the device 100 via the port 60 mounted on the cover 22 of the main housing 1 to a personal computer or other external device, or via the internet as previously described shown in FIG. 2. This allows the administrator/medical professional to store multiple sets of exercise data from multiple users. When this option is selected from the Main Menu 82, the user is prompted to either view set records for a specific saved set or transfer data out of the device 100 to an external computerized device. To view set records the user selects the desired set by pressing the left and right buttons 61. When the desired set of numbers is displayed, the user presses the select button to view the set results in the Track Progress 170 screens. On the Track Progress screens 170, the user is able to see the parameter data and quantitative data for each of the exercises completed. A point score is assigned to the user's performance. This is the proportional point score the user obtained while performing the exercises. Depending on how well a user performed an exercise, a score scaled out of a possible 100 points is displayed to the user on the Track Progress screens 170 following a completed exercise set. This score is generated using a calculated formula by the programmed exercise device microcontroller/microcomputer 300 that assigns a penalty score value for each failed attempt to stay within the specified parameters. The number of points deducted after the failures is a value that is proportionate to the number of total programmed exercise repetitions.

The user's results can be viewed at a later time by navigating through the menus to the View/Transfer Data menu 150. The user or administrator/medical professional can view the exercise by serial number. The results can then be downloaded in order to preserve the data for future reference into a patient's personal file. The data can be exported to an Excel Spreadsheet or any other kind of external database in, for example the health care provider computer, where it can be tabulated, manipulated, and displayed for interpretation/analysis. After the data is exported, the exercise device microcontroller/microcomputer memory component of the device 100 can be cleared so that data can be gathered on another user.

It will be appreciated by those skilled in the art that while the portable physical therapy/rehabilitation/exercise device, system and method 100 has been described in connection with particular embodiments and examples, the portable physical therapy/rehabilitation/exercise device system and method 100 is not necessarily so limited and that other examples, uses, modifications, and departures from the embodiments, examples, and uses may be made without departing from the portable physical therapy/rehabilitation/exercise device system and method 100. All these embodiments are intended to be within the scope and spirit of the appended claims.

What is claimed:

1. A portable physical therapy/rehabilitation/exercise device comprising:
    a main housing having a front side that defines a visual screen display opening, at least one control switch opening, at least one indicator light opening, and a main power switch opening;
    a removable cover that is attached to the main housing;
    a visual display screen disposed in the visual screen display opening; and,
    first and second handles that are connected to the main housing and extend from the main housing in opposite directions, and wherein the first handle is movable and extends and retracts relative to the main housing in a linear motion, and the second handle rotates about a central axis relative to the main housing and the first handle.

2. The portable physical therapy/rehabilitation/exercise device according to claim 1 further wherein the first handle includes a load cell outer tube, and a load cell inner tube disposed in the load cell outer tube inner tube, and a supporting housing positioned in the load cell inner tube and a load cell strain gauge disposed in the supporting housing and wherein the load cell housing provides for linear motion of the load cell strain gauge in order to detect movement of the first handle.

3. The portable physical therapy/rehabilitation/exercise device according to claim 2 wherein the alignment block is mounted to a ballnut mounting tube and a ballnut is disposed internal to the ballnut mounting tube and a ball screw is threaded to the ball nut, such that linear motion of load cell tube outer is converted to rotary motion of the ball screw.

4. The portable physical therapy/rehabilitation/exercise device according to claim 3 further including a first clutch assembly and wherein the rotary motion of the ball screw is transmitted to the first clutch assembly, and a first rotary encoder is connected to the ball screw and is capable of generating velocity and positional information pertaining to the load cell outer tube, and a programmed exercise device microcontroller/microcomputer for receiving the velocity and positional information pertaining to the load cell outer tube.

5. The portable physical therapy/rehabilitation/exercise device according to claim 2 wherein the first handle further includes a handgrip sensor having flexible handgrip strain gauges, and wherein the handgrip sensor is fitted on the load cell outer tube and for generating a signal when subjected to a compressive force.

6. The portable physical therapy/rehabilitation/exercise device according to claim 1 wherein a longitudinal axis extends though the device and the second handle is operatively associated with a ratchet mechanism such that the second handle allows for forward or reverse hand twisting action relative to the longitudinal axis.

7. The portable physical therapy/rehabilitation/exercise device according to claim 6 further including a second clutch assembly that is fed a variable voltage by a programmed exercise device microcontroller/microcomputer, and including a second rotary encoder that is connected in parallel with the second clutch assembly to provide the programmed exercise device microcontroller/microcomputer with velocity and positional feedback data, wherein disposed between the second clutch assembly and the second first handle is a torsion load cell and a gearbox and the gear box for translating the low speed, high torque rotational movement of the second first handle into a higher speed, lower torque rotational movement.

8. The portable physical therapy/rehabilitation/exercise device according to claim 7 further including torsional load cell mounted between the second clutch assembly and the main housing wherein the torsional load cell senses torque from the second clutch and converts the torque into an analog voltage that is then sent to the programmed exercise device microcontroller/microcomputer.

9. The portable physical therapy/rehabilitation/exercise device according to claim 1 further including an auxiliary load cell interface block that is disposed in the housing, and a hook attachment and a push pad attachment that are operatively associated with the an auxiliary load cell interface block.

10. The portable physical therapy/rehabilitation/exercise device according to claim 9 further including an auxiliary load cell that is connected to a mounting housing and the auxiliary load cell interface block, wherein the mounting housing prevents the rotation of auxiliary load cell alignment block such that the auxiliary load cell is only subjected to linear motion and the auxiliary load cell is capable of sending a voltage signal to a programmed exercise device microcontroller/microcomputer when a load is applied to a hook attachment or a push pad attachment.

11. The portable physical therapy/rehabilitation/exercise device according to claim 10 further wherein the main housing has a main housing interior and first and second angle sensors housings are disposed in the housing interior and each of the first angle sensor housings contain a pair of angle sensors and wherein the angle sensors sense angular input information of the main housing relative to gravity and relay this information to a programmed exercise device microcontroller/microcomputer such that the angular movement of a user of the device can be calculated by the programmed exercise device microcontroller/microcomputer.

12. A method for exercising for a using a portable physical therapy/rehabilitation/exercise device comprising the acts of:
providing a main housing and mounting first handle to the main housing that is linearly extendable and retractable relative to the main housing, and mounting a rotatable second handle to the main housing that extends in an opposite direction relative to the first handle and the second handle is rotatable about a central axis relative the main housing and the first handle and defining a housing interior in the main housing, mounting a visual display screen on the main housing, and providing a programmed exercise device microcontroller/microcomputer in the housing interior that is operatively associated with the first handle and the rotatable second handle and the visual display;
providing printed indicia on the visual display screen displaying the following modes of operation on the visual display screen:
evaluation mode,
manual exercise mode,
preset exercise mode,
manage settings mode, and,
view/transfer data mode, and,
selecting a mode of operation to commence an exercise session.

13. The method according to claim 12 further including the act of selecting the evaluation mode and selecting one of the following evaluations to assess the initial capabilities of a user:
stick evaluation and one of compression or tension;
twist evaluation and one of strength, dynamic strength, or range of motion;
handgrip evaluation;
static pull evaluation; and,
static push evaluation.

14. The method according to claim 12 further including the act of selecting the manual exercise mode and selecting one of the following exercises:
static stick exercise and one of either static compression or static tension;
dynamic stick exercise and one of either dynamic compression or dynamic tension;
static twisting exercise;
dynamic twisting exercise;
handgrip exercise;
static pull exercise; and,
dynamic pull exercise.

15. The method according to claim 12 further including the act of selecting the preset exercise mode and selecting one of the following exercises:
stick exercise;
static twist exercise;
dynamic twist exercise;
handgrip exercise;
static pull exercise rope; and,
dynamic pull exercise elastic stretch bands.

16. The method according to claim 12 further including further including a track progress option on the visual display screen such that a user has the option of viewing post-exercise feedback on the exercise repetitions performed.

17. A portable physical therapy/rehabilitation/exercise device comprising:
a main housing;
first and second handles that are connected to the main housing and extend from the main housing in opposite directions, and wherein the first handle is movable and extends and retracts relative to the main housing in a linear motion, and the second handle rotates about a central axis relative to the main housing and the first handle; and,
the first handle includes a load cell outer tube, and a load cell inner tube disposed in the load cell outer tube inner tube, and a supporting housing positioned in the load cell inner tube and a load cell strain gauge disposed in the supporting housing and wherein the load cell housing provides for linear motion of the load cell strain gauge in order to detect movement of the first handle; and,
wherein a longitudinal axis extends though the device and the second handle is operatively associated with a ratchet mechanism such that the second handle allows for forward or reverse hand twisting action relative to the longitudinal axis.

18. The portable physical therapy/rehabilitation/exercise device according to claim 17 wherein the first handle further includes a handgrip sensor having flexible handgrip strain gauges, and wherein the handgrip sensor is fitted on the load cell outer tube and for generating a signal when subjected to a compressive force.

* * * * *